United States Patent [19]
Larsen et al.

[11] Patent Number: 5,948,000
[45] Date of Patent: Sep. 7, 1999

[54] SYSTEM FOR SUTURE ANCHOR PLACEMENT

[75] Inventors: Scott Larsen, Newtown; Daniel R. Lee, Madison, both of Conn.

[73] Assignee: United States Surgical Corporation, Norwalk, Conn.

[21] Appl. No.: 08/919,900

[22] Filed: Aug. 28, 1997

Related U.S. Application Data

[63] Continuation of application No. 08/725,158, Oct. 3, 1996, abandoned.

[51] Int. Cl.[6] .................................................... A61B 17/00
[52] U.S. Cl. .............................. 606/232; 606/72; 606/80
[58] Field of Search .................................... 606/232, 144, 606/139, 148, 149, 72–75, 104, 96, 80

[56] References Cited

U.S. PATENT DOCUMENTS

| | | |
|---|---|---|
| 2,121,193 | 6/1938 | Hanicke . |
| 2,381,050 | 8/1945 | Hardinge . |
| 2,489,870 | 11/1949 | Dzus . |
| 2,490,364 | 12/1949 | Livingston . |

(List continued on next page.)

FOREIGN PATENT DOCUMENTS

| | | |
|---|---|---|
| 0019782 | 12/1980 | European Pat. Off. . |
| 075330 | 3/1983 | European Pat. Off. . |
| 0077868 | 5/1983 | European Pat. Off. . |
| 0 124 489 | 11/1984 | European Pat. Off. . |
| 0232049 | 1/1987 | European Pat. Off. . |

(List continued on next page.)

OTHER PUBLICATIONS

Raftopoulos, "A Proposed Design For An Expanding Hip Nail," Engineering in Medicine, vol. 11 (1982), pp. 187–188.

Design News, "Ligament Fastener Cuts Recovery Time," pp. 56–57, (1989).

Instrument Makar Inc., "The Ligamentous and Capsular Repair System", Arthroscopy Equipment and Supplies, Section One, p. 4.

Biomet Inc., "Ligament Screw System," 1990.

Arthrex, "The Complete Arthrex Information System."

Mitek Surgical Products, "Mitek GII Anchor, High Strength Fixation," 1991.

Mitek Surgical Products, "Mitek Anchor System, Effective Soft Tissue Reattachment," 1990.

Mitek Surgical Products, Mitek Quick Anchor, "Fast, Effective, Soft Tissue Reattachment," 1990.

Zimmer, Inc., "STATAK® Soft Tissue Attachment Device," 1988.

(List continued on next page.)

*Primary Examiner*—Michael Buiz
*Assistant Examiner*—Vikki Trinh

[57] ABSTRACT

A system for suture anchor placement includes an apparatus having a handle portion and an operating portion. The handle portion includes a spring, a needle park, and a member for releasably holding a length of the suture. The operating portion includes a sheath tube and a plunger rod slidably disposed within the bore of the sheath tube. The plunger rod is fixedly mounted at its proximal end to the handle. The suture anchor is releasably engaged to the distal end portion of the plunger rod. The sheath tube is mounted to the handle and movable with respect to the handle between a distal position and a proximal position, the sheath tube being resiliently biased to the distal position by the spring and movable to the proximal position in response to proximally directed force of sufficient magnitude applied to the distal end of the sheath tube. The sheath tube has a portion with an outer diameter greater than the diameter of the hole in the bone such that when the installation tool is pressed toward the bone, the sheath tube retracts into the handle and the suture anchor is advanced into a hole previously made in the bone. The suture, initially held in a taut configuration, is released in response to movement of the sheath tube to its proximal position.

22 Claims, 12 Drawing Sheets

U.S. PATENT DOCUMENTS

| | | |
|---|---|---|
| 2,579,438 | 12/1951 | Longfellow . |
| 2,699,774 | 1/1955 | Livingston . |
| 3,759,257 | 9/1973 | Fischer et al. . |
| 3,760,802 | 9/1973 | Fischer et al. . |
| 3,768,635 | 10/1973 | Eggert . |
| 3,779,239 | 12/1973 | Fischer et al. . |
| 3,782,374 | 1/1974 | Fischer . |
| 3,805,775 | 4/1974 | Fischer et al. . |
| 3,846,846 | 11/1974 | Fischer . |
| 3,910,281 | 10/1975 | Kletschka et al. . |
| 3,951,261 | 4/1976 | Mandel et al. . |
| 3,958,488 | 5/1976 | Fischer . |
| 3,986,504 | 10/1976 | Avila . |
| 4,006,747 | 2/1977 | Kronenthal et al. . |
| 4,013,071 | 3/1977 | Rosenberg . |
| 4,091,806 | 5/1978 | Aginsky . |
| 4,135,623 | 1/1979 | Thyen . |
| 4,204,531 | 5/1980 | Aginsky . |
| 4,227,518 | 10/1980 | Aginsky . |
| 4,236,512 | 12/1980 | Aginsky . |
| 4,244,370 | 1/1981 | Furlow et al. . |
| 4,259,072 | 3/1981 | Hirabayashi et al. . |
| 4,262,665 | 4/1981 | Roalstad et al. . |
| 4,275,717 | 6/1981 | Bolesky . |
| 4,309,137 | 1/1982 | Tanaka et al. . |
| 4,339,217 | 7/1982 | Lacey . |
| 4,351,069 | 9/1982 | Ballintyn et al. . |
| 4,409,974 | 10/1983 | Freedland . |
| 4,414,967 | 11/1983 | Shapiro . |
| 4,424,898 | 1/1984 | Thyen et al. . |
| 4,453,539 | 6/1984 | Raftopoulos et al. . |
| 4,454,875 | 6/1984 | Pratt et al. . |
| 4,456,005 | 6/1984 | Lichty . |
| 4,474,517 | 10/1984 | Navoczynski . |
| 4,483,678 | 11/1984 | Nishio et al. . |
| 4,519,100 | 5/1985 | Wills et al. . |
| 4,519,735 | 5/1985 | Mächtle . |
| 4,520,511 | 6/1985 | Gianezio et al. . |
| 4,539,981 | 9/1985 | Tunc . |
| 4,542,539 | 9/1985 | Rowe, Jr. et al. . |
| 4,550,448 | 11/1985 | Kenna . |
| 4,550,449 | 11/1985 | Tunc . |
| 4,570,623 | 2/1986 | Ellison et al. . |
| 4,586,502 | 5/1986 | Bedi et al. . |
| 4,590,928 | 5/1986 | Hunt et al. . |
| 4,590,930 | 5/1986 | Kurth et al. . |
| 4,591,048 | 5/1986 | Eldridge, Jr. . |
| 4,596,503 | 6/1986 | Mirsberger et al. . |
| 4,599,085 | 7/1986 | Riess et al. . |
| 4,612,923 | 9/1986 | Kronenthal . |
| 4,621,640 | 11/1986 | Mulhollan et al. . |
| 4,632,100 | 12/1986 | Somers et al. . |
| 4,637,765 | 1/1987 | Omata . |
| 4,640,271 | 2/1987 | Lower . |
| 4,653,486 | 3/1987 | Coker . |
| 4,655,777 | 4/1987 | Dunn et al. . |
| 4,656,806 | 4/1987 | Leibhard et al. . |
| 4,669,473 | 6/1987 | Richards et al. . |
| 4,681,590 | 7/1987 | Tansey . |
| 4,699,271 | 10/1987 | Lincoln et al. . |
| 4,711,232 | 12/1987 | Fischer et al. . |
| 4,713,076 | 12/1987 | Draenert . |
| 4,716,893 | 1/1988 | Fischer et al. . |
| 4,738,255 | 4/1988 | Goble et al. . |
| 4,741,330 | 5/1988 | Hayhurst . |
| 4,759,670 | 7/1988 | Linder et al. . |
| 4,760,843 | 8/1988 | Fischer et al. . |
| 4,767,248 | 8/1988 | Pratt . |
| 4,776,328 | 10/1988 | Frey et al. . |
| 4,776,329 | 10/1988 | Treharne . |
| 4,778,468 | 10/1988 | Hunt et al. . |
| 4,787,378 | 11/1988 | Sodhi . |
| 4,790,303 | 12/1988 | Steffee . |
| 4,790,304 | 12/1988 | Rosenberg . |
| 4,793,335 | 12/1988 | Frey et al. . |
| 4,796,612 | 1/1989 | Reese . |
| 4,806,053 | 2/1989 | Herb . |
| 4,818,163 | 4/1989 | Bereiter et al. . |
| 4,828,562 | 5/1989 | Kenna . |
| 4,834,752 | 5/1989 | Van Kampen . |
| 4,861,197 | 8/1989 | Calandra, Jr. . |
| 4,870,957 | 10/1989 | Goble et al. . |
| 4,871,289 | 10/1989 | Choiniere . |
| 4,895,148 | 1/1990 | Bays et al. . |
| 4,898,156 | 2/1990 | Gatturna et al. . |
| 4,898,505 | 2/1990 | Froehlich . |
| 4,899,743 | 2/1990 | Nicholson et al. . |
| 4,921,383 | 5/1990 | Fischer . |
| 4,927,421 | 5/1990 | Goble et al. . |
| 4,938,760 | 7/1990 | Burton et al. . |
| 4,946,468 | 8/1990 | Li . |
| 4,963,144 | 10/1990 | Huene . |
| 4,968,315 | 11/1990 | Gatturna . |
| 4,969,887 | 11/1990 | Sodhi . |
| 4,969,892 | 11/1990 | Burton et al. . |
| 4,976,680 | 12/1990 | Hayman et al. . |
| 4,976,715 | 12/1990 | Bays et al. . |
| 4,988,351 | 1/1991 | Paulos et al. . |
| 5,002,550 | 3/1991 | Li . |
| 5,011,473 | 4/1991 | Gatturna . |
| 5,013,316 | 5/1991 | Goble et al. . |
| 5,015,250 | 5/1991 | Foster . |
| 5,036,862 | 8/1991 | Pohndorf . |
| 5,037,422 | 8/1991 | Hayburst . |
| 5,041,129 | 8/1991 | Hayburst et al. . |
| 5,046,513 | 9/1991 | Gatturna et al. . |
| 5,053,047 | 10/1991 | Yoon . |
| 5,071,420 | 12/1991 | Paulos et al. . |
| 5,076,746 | 12/1991 | Fischer et al. . |
| 5,078,730 | 1/1992 | Li et al. . |
| 5,080,543 | 1/1992 | Murphy . |
| 5,084,050 | 1/1992 | Draenert . |
| 5,085,545 | 2/1992 | Takahashi . |
| 5,085,661 | 2/1992 | Moss . |
| 5,100,405 | 3/1992 | McLaren . |
| 5,100,417 | 3/1992 | Cerier et al. . |
| 5,102,421 | 4/1992 | Anspach, Jr. . |
| 5,122,133 | 6/1992 | Evans . |
| 5,129,906 | 7/1992 | Ross et al. . |
| 5,131,533 | 7/1992 | Alpern . |
| 5,144,961 | 9/1992 | Chen et al. . |
| 5,154,719 | 10/1992 | Cotrel . |
| 5,156,616 | 10/1992 | Meadows et al. . |
| 5,167,664 | 12/1992 | Hodorek . |
| 5,167,665 | 12/1992 | McKinney . |
| 5,176,682 | 1/1993 | Chow . |
| 5,203,784 | 4/1993 | Ross et al. . |
| 5,207,679 | 5/1993 | Li ................................. 606/72 |
| 5,209,753 | 5/1993 | Biedermann et al. . |
| 5,217,486 | 6/1993 | Rice et al. . |
| 5,224,946 | 7/1993 | Hayhurst et al. . |
| 5,236,445 | 8/1993 | Hayhurst et al. . |
| 5,246,441 | 9/1993 | Ross et al. . |
| 5,258,016 | 11/1993 | DiPoto et al. . |
| 5,268,001 | 12/1993 | Nicholson et al. . |
| 5,336,240 | 8/1994 | Metzler et al. . |
| 5,354,298 | 10/1994 | Lee et al. ................... 606/72 |
| 5,423,860 | 6/1995 | Lizardi et al. . |
| 5,441,502 | 8/1995 | Bartlett ..................... 606/104 |
| 5,480,403 | 1/1996 | Lee et al. . |
| 5,522,844 | 6/1996 | Johnson . |
| 5,531,699 | 7/1996 | Tomba et al. ............ 604/164 |

| | | |
|---|---|---|
| 5,534,011 | 7/1996 | Greene, Jr. et al. . |
| 5,578,057 | 11/1996 | Wenstrom et al. ............... 606/232 |
| 5,584,860 | 12/1996 | Goble et al. . |
| 5,628,751 | 5/1997 | Sander et al. . |
| 5,643,320 | 7/1997 | Lower et al. . |
| 5,662,658 | 9/1997 | Wenstrom, Jr. . |
| 5,667,513 | 9/1997 | Torrie et al . |
| 5,707,394 | 1/1998 | Miller et al. ..................... 606/232 |
| 5,741,268 | 4/1998 | Schütz . |

FOREIGN PATENT DOCUMENTS

| | | |
|---|---|---|
| 0 232 049 | 8/1987 | European Pat. Off. . |
| 0230937 | 8/1987 | European Pat. Off. . |
| 0238223 | 9/1987 | European Pat. Off. . |
| 0241240 | 10/1987 | European Pat. Off. . |
| 0 270 704 | 6/1988 | European Pat. Off. . |
| 0376641 | 7/1990 | European Pat. Off. . |
| 0409364 | 1/1991 | European Pat. Off. . |
| 0464479 | 1/1992 | European Pat. Off. . |
| 0464480 | 1/1992 | European Pat. Off. . |
| 0465910 | 1/1992 | European Pat. Off. . |
| 0 502 509 A1 | 9/1992 | European Pat. Off. . |
| 504 915 A1 | 9/1992 | European Pat. Off. . |
| 0 588 671 A1 | 3/1994 | European Pat. Off. . |
| 0 630613 | 12/1994 | European Pat. Off. . |
| 739089 | 1/1933 | France . |
| 2622430 | 5/1989 | France . |
| 3445738 | 6/1986 | Germany . |
| 3509417 | 9/1986 | Germany . |
| 8633339 | 4/1987 | Germany . |
| 4106823 | 6/1992 | Germany . |
| 584855 | 12/1977 | U.S.S.R. . |
| 2084468 | 9/1981 | United Kingdom . |
| 2 199 914 | 7/1988 | United Kingdom . |
| 2 266 246 | 10/1993 | United Kingdom . |
| WO 85/04568 | 10/1985 | WIPO . |
| WO8603666 | 7/1986 | WIPO . |
| WO 89/01767 | 3/1989 | WIPO . |
| WO8909030 | 10/1989 | WIPO . |
| WO8910096 | 11/1989 | WIPO . |
| WO9204874 | 4/1992 | WIPO . |
| WO93/08747 | 5/1993 | WIPO . |
| WO9515726 | 7/1995 | WIPO . |
| WO 96/14798 | 5/1996 | WIPO . |

OTHER PUBLICATIONS

Acufex Microsurgical Inc., "TAG® Tissue Anchor Guide System."

Acufex Microsurgical Inc., "Technique for Using the TAG® Tissue Anchor—Rod Style."

Acufex Microsurgical Inc., "Technique for Using the TAG® Tissue Anchor—Wedge Style."

Assembly Engineering, "Special Blind Rivets," 1979.

K. Hoffer, Bremen, Rivet Joints in Aluminum Structural Components (1), vol. 59, 1983.

SYSTEM FOR SUTURE ANCHOR PLACEMENT

This is a continuation of application Ser. No. 08/725,158 filed Oct. 3, 1996 abandoned.

BACKGROUND

1. Technical Field

The present disclosure relates to a suture anchor installation system and, more particularly, to a system for preparing a hole in hard tissue to receive the suture anchor and for insertion therein of a suture anchor.

2. Discussion of Related Art

During surgery, it is often necessary to attach muscle tissue or prosthetic implants to hard tissue such as bone. Suture anchors are used in the art to facilitate such attachment by securing a suture to bone. Generally, an anchor is implanted into a hole pre-drilled into a bone mass. A suture engaged by the suture anchor extends from the bone and is used to stitch the muscle tissue or prosthetic device to the bone. Suture anchors find particular use in joint reconstruction surgery, especially during attachment of ligaments or tendons to bones in the knee, shoulder, and elbow.

Several systems have been proposed in the art to aid the surgeon in implanting a suture anchor into a bone. One such system, shown in U.S. Pat. No. 5,100,417 to Cerier et al., includes a driver having a handle and elongated shaft. An anchor snap fits on the end of the shaft over an anti-rotation pin which mates with slots in the anchor. A suture engaged in the anchor has its ends affixed to posts extending from the driver handle. The Cerier et al. system suffers from the disadvantage that the driver does not accommodate sutures having preattached needles. Thus, use of this system requires threading the suture into a needle, a time-consuming procedure for the surgeon.

Another suture anchor installation system is shown in U.S. Pat. No. 5,002,550 to Li. The Li system includes a suture anchor having a normally curved barb capable of being elastically deformed to a substantially straight configuration. The suture anchor engages a suture having a pair of surgical needles attached to its ends. The installation tool is adapted to receive the surgical needles and a pair of grooves formed in the tool's outer surface. The tool additionally provides a member for selectively covering and uncovering the needles received in the grooves. The Li suture anchor installation system uses shape-memory alloys to fabricate the suture anchors. Such materials are not bioabsorbable. Additionally, the normally curved barb of the Li system protrudes from the installation tool during positioning of the anchor.

Yet another suture anchor installation system is disclosed in U.S. Pat. No. 5,354,298 to Lee et al. The suture anchor installation system includes a suture anchor assembly engaged with a suture anchor insertion tool. The suture anchor assembly features a two-piece suture anchor for insertion into a predrilled hole in a bone and at least one suture having at least one surgical needle affixed thereto. The two-piece suture anchor has a setting pin slidably engaged within an engagement member having barbed legs expandable in response to proximal movement of the setting pin. The suture anchor insertion tool includes a body portion and a distally extending shaft portion. An annular region of the distal end of the shaft portion engages the legs of the suture anchor engagement member. A channel in the shaft portion aligns with a channel in the body portion to accommodate the suture. Needle-retaining assemblies located on the body portion of the suture anchor insertion tool engage the surgical needle or needles attached to the suture. The suture anchor installation tool of the Lee et al. U.S. Pat. No. 5,354,298 patent is packaged in a preloaded condition. The package is opened in the operating room and the installation tool is removed from the package and used to apply the suture anchor.

What is needed is an improved system which facilitates implantation of the suture anchor into hard tissue such as, e.g., bone.

SUMMARY

A suture anchor installation system is provided herein, the system including a drill and drill guide, an obturator, at least one suture anchor and a suture anchor installation tool. The suture anchor includes an elongated setting pin at least partially mounted within a longitudinal bore of a socket and slidably movable between a distal first position wherein at least a portion of the setting pin is distal to the socket and a proximal second position. A suture is disposed through a hole in the setting pin. The socket has at least two proximally pointing legs which are radially expandable in response to movement of the setting pin to the proximal second position.

The suture anchor installation tool includes a handle portion including a spring, and an elongated operating portion. The operating portion includes a sheath tube having an axial bore and distal and proximal ends, and an inner rod slidably disposed within the bore of the sheath tube. The inner rod is fixedly mounted to the handle, while the sheath tube is movably mounted to the handle, the sheath tube being movable with respect to the handle between a distal position and a proximal position, and being resiliently biased to the distal position by the spring. Application of a proximally directed force of sufficient magnitude to the distal end of the sheath tube causes the sheath tube to move to the proximal position against the biasing force of the spring.

In the initial configuration the suture is held taut by the installation tool, which also includes at least one pinch means for releasably holding a suture, the pinch means frictionally holding the suture when the sheath tube is in the distal position and releasing the suture in response to movement of the sheath tube to the proximal position. The pinch means is of a plate and a member having at least one leg in opposing relation to the plate, the leg being biased toward the plate to hold a suture therebetween when the sheath tube is in the distal position, and the leg resiliently moving away from the wall in response to movement of the sheath tube to the proximal position.

Also disclosed herein is a method for employing the suture anchor installation system to apply a suture anchor to a bone mass.

BRIEF DESCRIPTION OF THE DRAWINGS

Various embodiments are described below with reference to the drawings wherein.

DETAILED DESCRIPTION OF PREFERRED EMBODIMENTS

The suture anchor installation system described herein is provided for securing a suture to bone. The suture can be used to attach soft tissue or a prosthetic device to the bone. As used herein, the term "soft tissue" refers to all of the non-bony tissues within an organism including, but not limited to, muscle, cartilage, skin, tendons, ligaments, etc. The term "prosthetic device" refers to any article implanted in the body including, but not limited to, artificial ligaments, muscles, joints, etc.

The suture anchor installation system can be used in minimally invasive surgical procedures. In such procedures the operating instrumentation is deployed through a cannula inserted through a small incision or opening in a wall of body tissue (e.g. the skin and underlying tissue), or directly through the incision or opening itself. Such procedures include laparoscopic, endoscopic, and arthroscopic surgical operations. In operations where, for example, a body cavity is insufflated to provide a clear operating field, gaseous seals are usually employed to prevent the inflow or egress of fluids into or out from the operating site. It should be understood that the suture anchor installation system is not limited to minimally invasive procedures, and can be used in open surgical procedures as well.

The suture anchor installation system described herein includes a suture anchor assembly retained in a suture anchor insertion tool. The suture anchor assembly features a two-piece suture anchor for insertion into a pre-drilled hole in bone and at least one suture having at least one surgical needle affixed thereto. The two-piece suture anchor includes a setting pin slidably engaged within an expandable engagement member which grips the sides of the hole which has been drilled in the bone. In a preferred embodiment, this engagement member is an expandable socket, which includes an apertured body portion having at least two barbed legs extending proximally therefrom. The legs are radially expandable in response to proximal movement of the setting pin. Suture anchors suitable for use in the suture anchor installation system described herein are described in U.S. Pat. No. 5,354,298. The suture can be "double-armed", i.e. a needle can be attached to each of the two ends of the suture to facilitate knotting the suture and securing the soft tissue to the bone.

Figure 1:
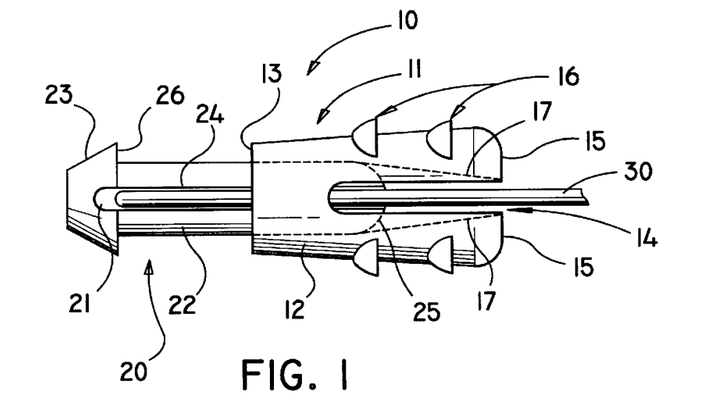
FIG. 1 is a side view of a suture anchor for use in the current disclosure.
Figures 2, 3:
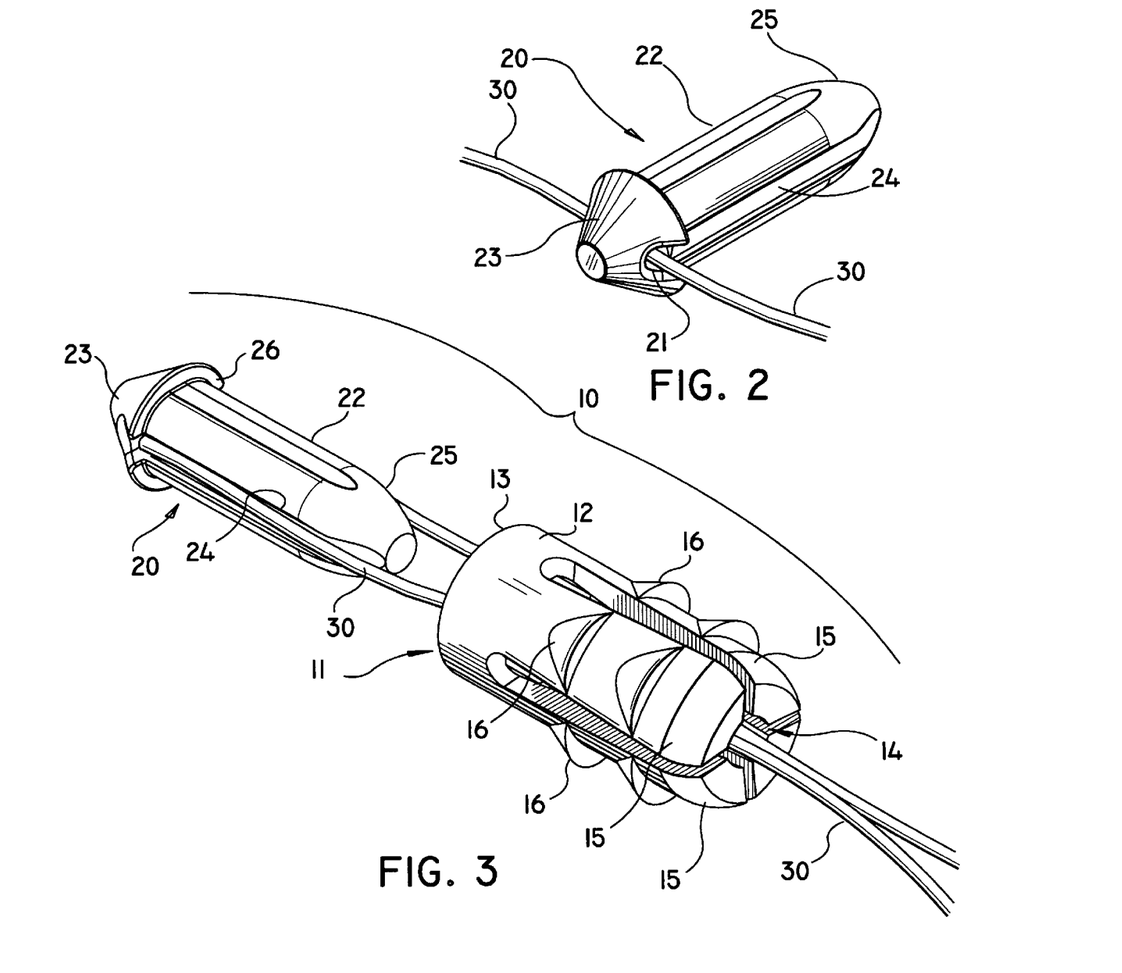
FIG. 2 is a perspective view of the setting pin of the suture anchor with a suture disposed therethrough.
FIG. 3 is an exploded view showing the suture retained by the suture anchor.

More particularly, referring now to FIGS. 1 to 3, a preferred two-piece suture anchor 10 is illustrated. Preferably, the suture anchor 10 is fabricated from a synthetic bioabsorbable polymeric resin such as polymers of glycolide, lactide, caprolactone, p-dioxanone, trimethylene carbonate and physical and/or chemical combinations thereof. The suture is preferably a size 2 suture formed of Dacron. However, it is anticipated that the suture may also be formed from a synthetic bioabsorbable polymeric resin.

The suture anchor 10 includes a socket 11 for insertion distally into a pre-drilled hole in bone or hard tissue. The socket has a body portion 12 terminating in an annular distal end surface 13 which acts as a stop surface as discussed below, an axially extending aperture 14, and at least two (preferably four) legs 15 extending proximally from the body portion 12. Legs 15 are normally radially expandable in response to movement of a setting pin 20 slidably disposed within the axially extending aperture 14. Setting pin 20 has a suture attachment feature and is movable between a distal position with respect to socket 11 wherein socket legs 15 are not expanded, and a proximal position with respect to the socket 11 wherein the socket legs 15 are urged to a radially spread-out configuration.

More particularly, setting pin 20 includes a shaft portion 22, a tapered tip 23 with preferably a frustoconical shape and a proximal facing abutment surface 26, and a transverse aperture 21 near the distal end for receiving a suture 30. Proximal end 25 is rounded and acts as a camming surface. Setting pin 20 also includes two longitudinal notches 24 extending along shaft portion 22 through which suture 30 is disposed.

Proximally extending legs 15 of socket 11 include barbs 16 on their outer surface and an inwardly inclined inner surface 17. When setting pin 20 is moved proximally from its initial distal-most position (i.e. by pulling suture 30), the rounded proximal end 25 of the shaft portion cams against inner surface 17 and thereby urges legs 15 to expand radially outward. At the most proximal position of setting pin 20, abutment surface 26 of tapered tip 23 contacts distal end surface 13 of the socket. The Setting pin 20 is thereby stopped from further proximal movement. A matching non-circular cross section of the setting pin and the socket aperture may be employed to prevent suture interference with the setting action by preventing free rotation of the setting pin within the axial aperture of the socket and by locating the suture between legs 15 of socket 11.

Figure 4:
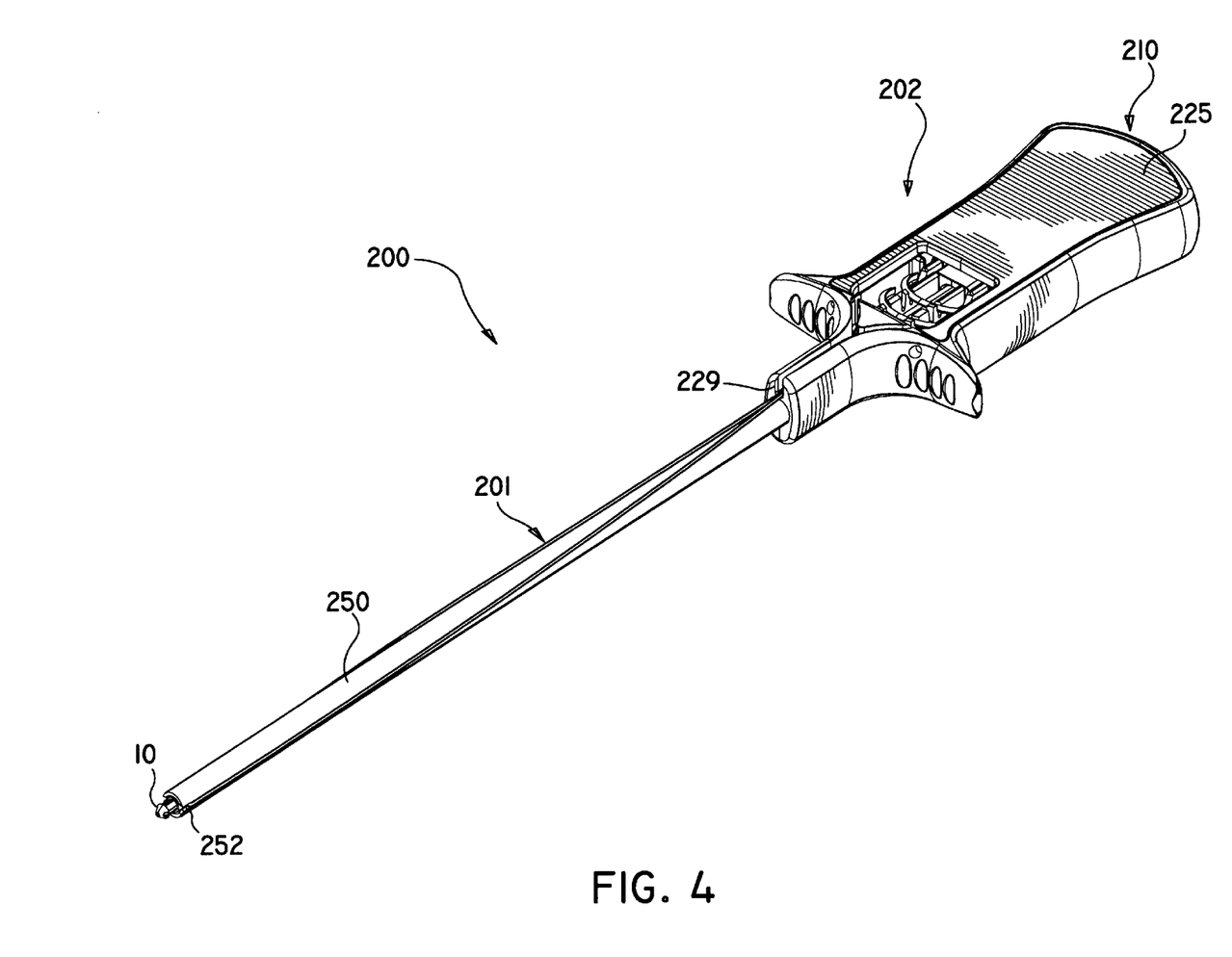
FIG. 4 is a perspective view of the suture anchor installation tool.
Figure 5:
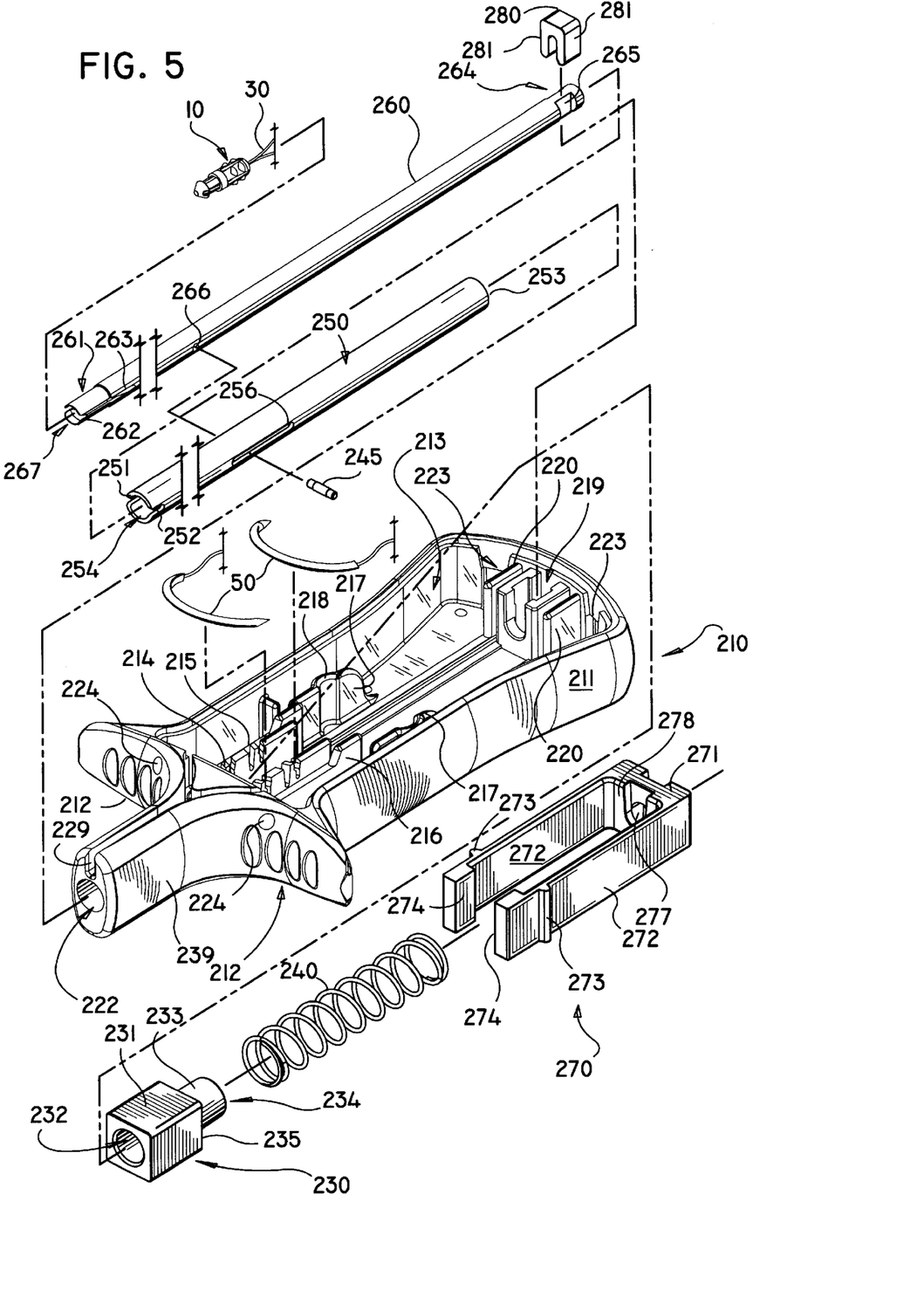
FIG. 5 is an exploded view of the suture anchor installation tool with suture anchor and needles.

Referring now to FIGS. 4 and 5, the suture anchor installation system includes an installation tool 200 having an elongated operating portion 201 and a handle portion 202. The elongated operating portion 201 includes an outer sheath tube 250 and a plunger rod 260.

Figures 6, 7, 8:
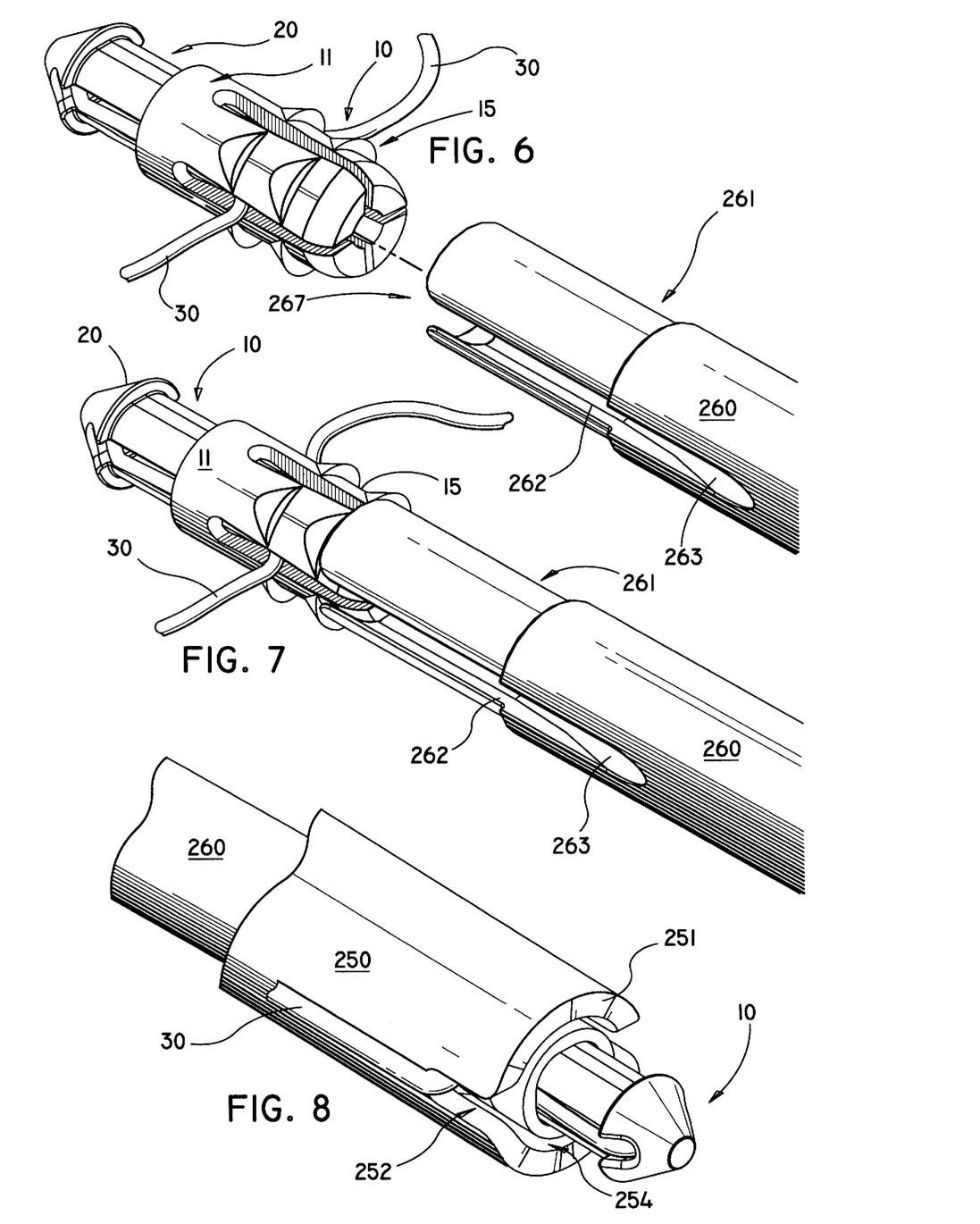
FIGS. 6 and 7 are perspective views illustrating positioning of the suture anchor at the distal end of the plunger rod.
FIG. 8 is a perspective view illustrating the positioning of the suture anchor at the distal end of the installation tool.

Sheath tube 250 is slidably connected to handle 210 and has an axial bore 254, a distal end 251 with lengthwise slots 252 positioned in the vicinity of the distal end 251, and a proximal end 253. The distal end of the sheath tube acts as the primary support for the suture anchor 10. Referring to FIGS. 4 and 8, slots 252 provide access for suture 30 to exit from the interior of bore 254 and extend along the outer surface of sheath tube 250 to handle 210. Referring again to FIG. 5, the proximal end 253 of sheath 250 tube abuts a cam cap 230, the function of which is explained below. Longitudinal slot 256 in the sheath is adapted to receive plunger pin 245 and acts as a motion limiter, as explained below.

Referring to FIGS. 5–7, plunger rod 260 is slidably disposed within bore 254 of sheath tube 250, and includes a distal end portion 261 which includes opening 267 to releasably engage the proximal end portion of legs 15 of the suture anchor 10, and two slots 262 which permit passage therethrough of the suture 30. Notches 263 extend longitudinally from the proximal ends of slots 262 to facilitate the doubling back of suture 30 and allow the suture to extend distally outward and through slots 252 in the sheath tube (See, FIG. 8) Proximal end portion 264 includes notches 265 which are engaged by a plunger retainer block 280 (FIG. 7). Plunger retainer block 280 is received into a plunger retainer frame 219 in the interior chamber 213 of handle 210, and fixedly connects plunger rod 260 to handle 210. Plunger rod 260 includes a lateral aperture 266 to receive plunger pin 245. Plunger pin 245 extends laterally into slot 256 of sheath tube 250 to limit the relative longitudinal motion between plunger rod 260 and sheath tube 250. For example, if outer sheath tube 250 moves proximally with respect to plunger rod 260, plunger pin 245 abuts the distal edge of slot 256 after sheath tube 250 has moved a certain distance. Further relative movement is thereby prohibited in that direction.

Referring to FIGS. 5–11, handle portion 202 includes a handle 210, which has, inter alia, a body portion 211 serving as a hand grip, a finger rest 212, and a cover plate 225. Body portion 211 and cover plate 225 define an interior chamber 213. Longitudinal aperture 222 extends through nose portion 239 of handle body portion 211 and is adapted to receive sheath tube 250 and plunger rod 260. The nose portion 239 also includes a Y-shaped notch 229 which serves as a suture track. That is, suture 30 extends along sheath 250 from slot 252 to interior chamber 213 and is disposed through notch 229 such that one length of suture 30 passes through one branch of Y-shaped notch 229 and the other length of the suture 30 passes through the other branch of Y-shaped notch 229.

Handle body portion 211 includes lengthwise spaced apart needle park plates 214 having needle retaining notches 215. Notches 215 are adapted to releasably hold a surgical needle in a snap fit arrangement. Needle park plates 214 are preferably parallel to each other each having two sets of notches such that at least two needles 50 can be releasably held by the plates. As can be seen, the needles extend laterally across the top of plates 214, each needle being held in one set of notches 215 in each plate 214.

Guide plates 216 are preferably oriented parallel to the needle park plates 214 and provide a guide surface for the suture lengths 30 entering interior chamber 213 from Y-shaped notch 229. The guide plates also stabilize the needles 50 to allow for closer placement.

Pinch plates 217 are spaced apart from each other and the space between them provides a reception area to receive pinch block 270. The suture lengths 30 are guided by guide plates 216 to enter the space between pinch plates 217 and pinch block 270 (discussed below). Pinch plates 217 each have a curved portion 218 which provides a suture pinch area.

Needle park plates 214, guide plates 216, pinch block plates, buttress plates 220 and 221 (discussed below), and plunger block retainer frame 219, are features which may be integrally fabricated as part of handle body 211 by, for example, molding body portion 211 from a suitable material, such as polycarbonate, acrylics, or other synthetic polymeric resins. Handle body 211 also includes apertures 224 to receive alignment rods 228 in the cover.

Pinch block 270 is a single piece generally U-shaped body which includes parallel legs 272 extending distally from a proximal wall 271 and terminating in opposing jaws 274. Jaws 274 define between them a space for the reception of cam cap 230. Legs 272 are resiliently movable toward or away from each other to vary the distance between jaws 274. A ridge 273 extends vertically (as shown) on an outer surface of each leg 272, the ridge being received into curved suture pinch areas 218 of pinch plates 217. When legs 272 are biased outward, ridges 273 and respective suture pinch areas 218 close upon the suture portion disposed between them, thereby frictionally holding the suture.

Pinch block 270 also includes an axial aperture 277 in proximal wall 271 through which plunger rod 260 is disposed. The distal surface 278 of the proximal wall provides an abutment surface for helical compression spring 240, which is positioned between legs 272. Pinch block 270 is securely retained in interior chamber 213 between buttress plates 220 and guide plates 216.

Cam cap 230 includes a single piece structure including a rectangular distal portion 231 having an internal cylindrical bore 232, and a cylindrical proximal portion 233 having bore 234. Cam cap 230 possesses an exterior proximally facing surface 235 which provides an abutment for spring 240. Also, a distally facing annular surface 236 in internal cylindrical bore 232 provides an abutment for proximal end 253 of the sheath tube. Thus, sheath tube 250 is inserted into cylindrical bore 232, and spring 240 is mounted around proximal portion 233. The plunger rod 260 extends through bore 234.

Cam cap 230 is initially positioned such that distal portion 231 is between jaws 274 of pinch block 270, thereby biasing legs 272 outward to frictionally secure suture lengths 30 between ridges 273 and pinch areas 218 of pinch plates 217. When sheath tube 250 is moved proximally, cam cap 230 is forced against the biasing action of compression spring 240 into the space between legs 272. This allows legs 272 to resiliently bend inward to a degree sufficient to release the suture lengths 30. Also, because jaws 274 move inwardly, cam cap 230, once past the jaws, cannot return distally to its initial position between the jaws. Thus, once the outer sheath is retracted beyond a predetermined distance it remains in the retracted configuration and cannot move distally forward to its initial position.

Plunger retainer block 280 includes leg members 281 which engage notches 265 in plunger rod 260. Plunger retainer block 280 is adapted to fit into retainer frame 219 so as to secure the proximal end portion 264 of plunger rod 260 to handle 210.

Buttresses 220 are plates which extend longitudinally along side retainer frame 219. Buttresses 221 are plates which extend laterally from the inner wall of body grip 211 in the vicinity of the pinch plates 217. Both serve as reinforcements and are preferably an integral part of handle body 211.

Figure 9:
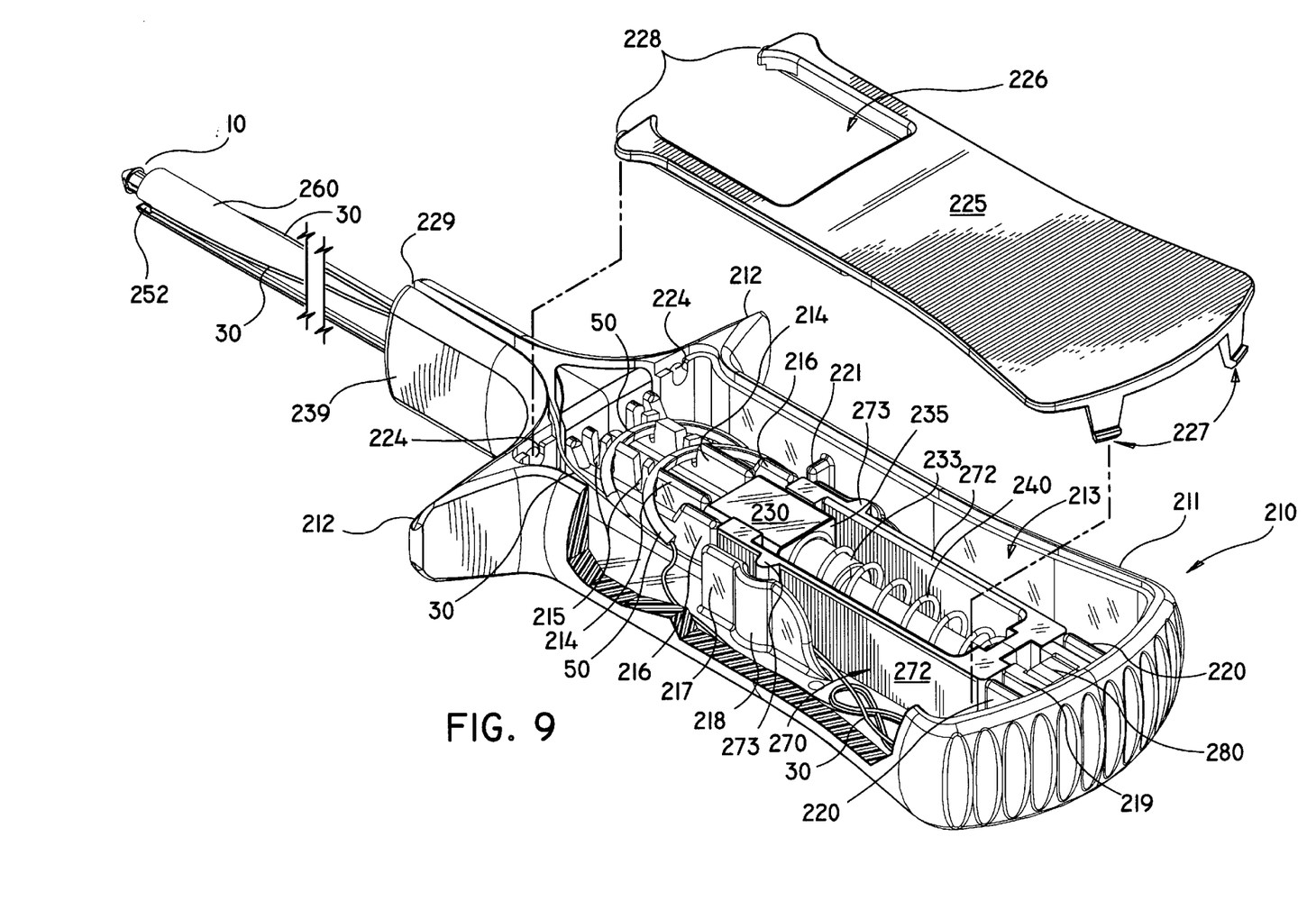
FIG. 9 is a partial cut away exploded perspective view of the handle portion of the suture anchor installation tool.
Figure 10:
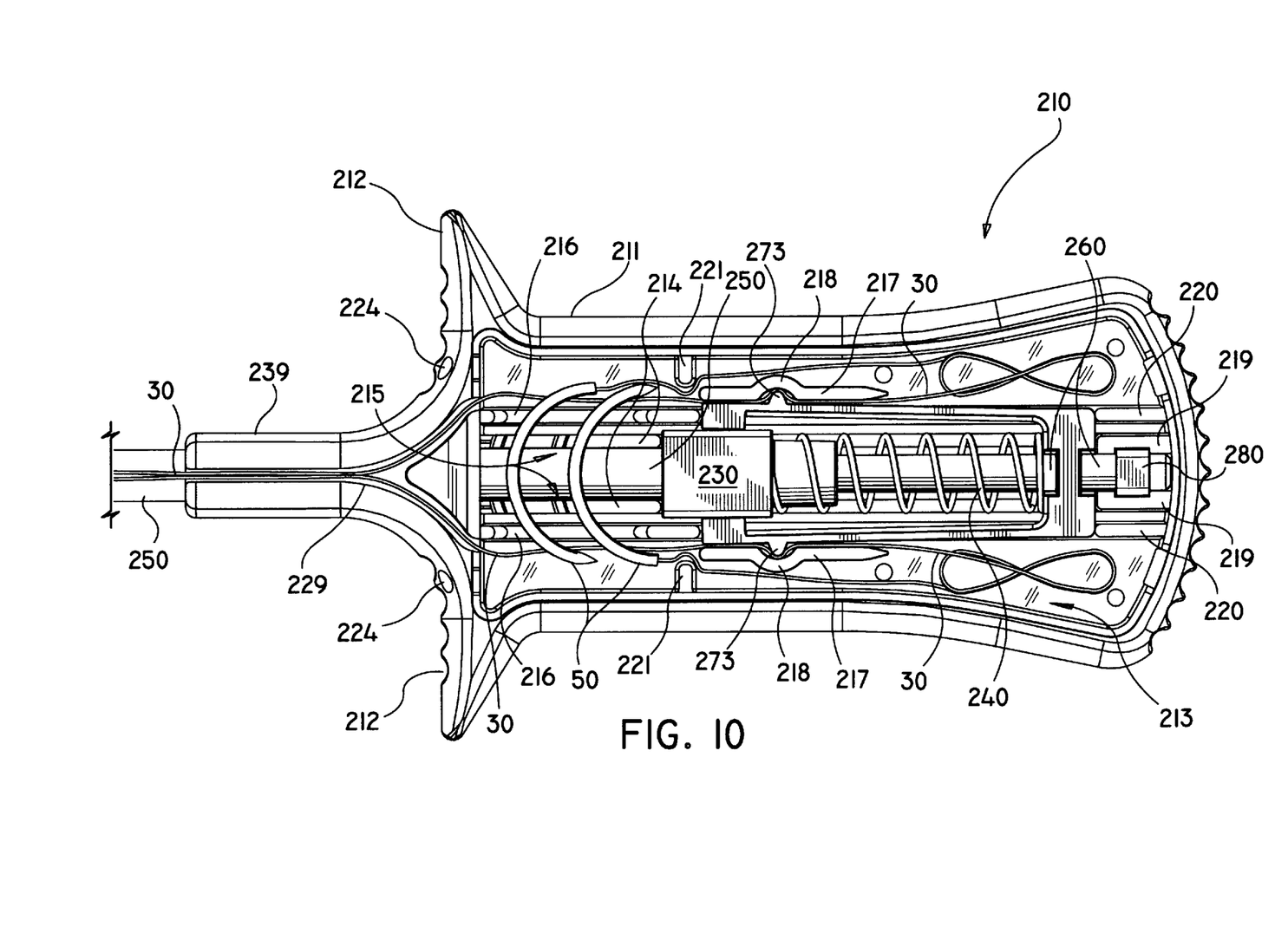
FIG. 10 is a top view of the handle portion of the suture anchor installation tool.
Figure 11:
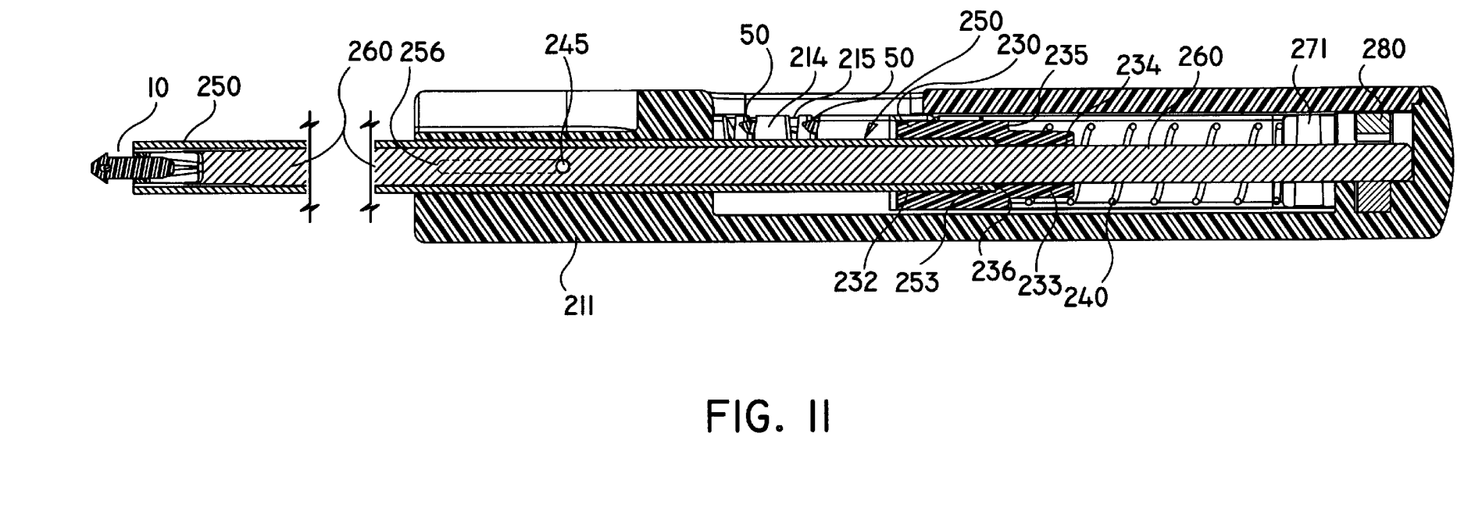
FIG. 11 is a side sectional view of the handle portion of the suture anchor installation tool.

Referring to FIG. 9, cover 225 is a flat plate which includes distally extending alignment rods 228, resilient hooks 227, and an open window area 226. Alignment rods 228 are adapted to fit into aperture 224 in the body grip. The hooks 227 are adapted to engage catches 223 in the body grip in a snap-fit manner.

Figures 12, 13, 14:
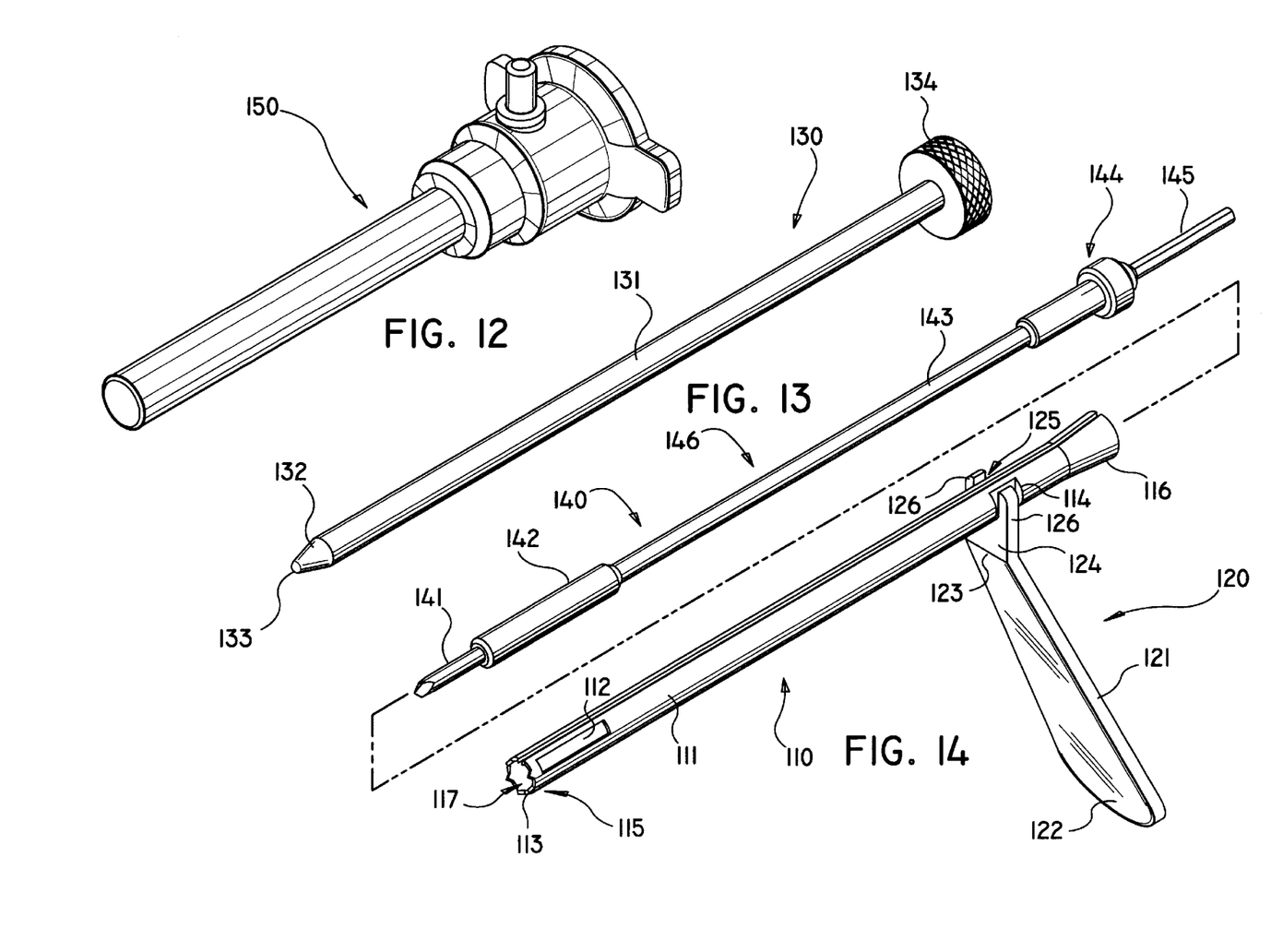
FIG. 12 is a perspective view of a cannula.
FIG. 13 is a perspective view of an obturator.
FIG. 14 is an exploded perspective view of the drill bit and drill guide.

Referring now to FIGS. 12 to 14, the suture anchor installation system includes a drill guide 110, drill bit 140, and obturator 130, all adapted to fit within the bore of a standard cannula 150. Means is provided herein for drilling a hole in bone. The drilling means includes the drill guide 110 and the drill bit 140.

Referring to FIG. 14, drill guide 110 provides precise positioning of the drill for drilling a hole for the suture anchor into the mass of bone tissue, and is a tubular body 111 having teeth 113 for gripping bone tissue at its distal end 115, and, optionally, flat surfaces 114 spaced apart from the flared proximal end portion 116. Axial bore 117 in the drill guide is adapted to receive a drill bit 140, discussed below. At least one, and preferably two or three, openings 112 in the vicinity of the distal end 115 permit the escape of bone fragments and shavings during the drilling operation and also permit visualization of the drill bit placement by the surgeon. The flat surfaces 114 are adapted to engage slot 125 in the forked end portion 124 of a handle 120. Drill guide 110 is preferably fabricated from a biocompatible metal such as stainless steel alloy.

Drill guide handle 120 is fixedly attached to drill guide 110 to facilitate the surgeon's handling of drill guide 110. Drill guide handle 120 is a single piece composed of a grasping plate 121 having a wide end portion 122 adapted to facilitate manual gripping by the surgeon. The forked end portion 124 includes two parallel spaced apart prongs 126 which define a slot 125 between them into which the drill guide 110 is engaged at the flat surfaces 114. The forked end portion 124 is connected to the grasping plate 121 at angled bend 123.

Drill bit 140 is used to create a hole of predetermined diameter in the mass of bone tissue. Drill bit 140 is a single piece member having a distal drilling tip 141, a shaft 146 having a relatively wide distal portion 142, a relatively narrow mid portion 143, and a proximal portion 144. A shank 145 extends proximally from portion 144 of shaft 146 and is adapted to engage the chuck of a drilling machine (not shown). Drilling machines suitable for use in rotating the drill bit are well known and available to those with skill in the art. The drill bit 140 is adapted to fit into bore 117 of drill guide 110 and to be able to rotate therein.

Referring to FIG. 13, obturator 130 is part of the suture anchor installation system and includes a shaft 131 having a bevelled tip 132 with rounded point 133. A knurled knob 134 facilitates its handling and use to create a puncture opening in the soft body tissue overlying the bone with minimal damage to the body tissue.

Referring to FIG. 12, a cannula 150 suitable for use in the present system is shown. Such cannulas are well known in the art and widely available.

Referring to FIGS. 15 to 18 the use of the suture anchor installation system is illustrated.

First, an incision 71 is created in the skin and access to body tissue 70 surrounding the bone at the operating site is achieved. Cannula 150 is inserted into the incision 71.

Figures 15, 16:
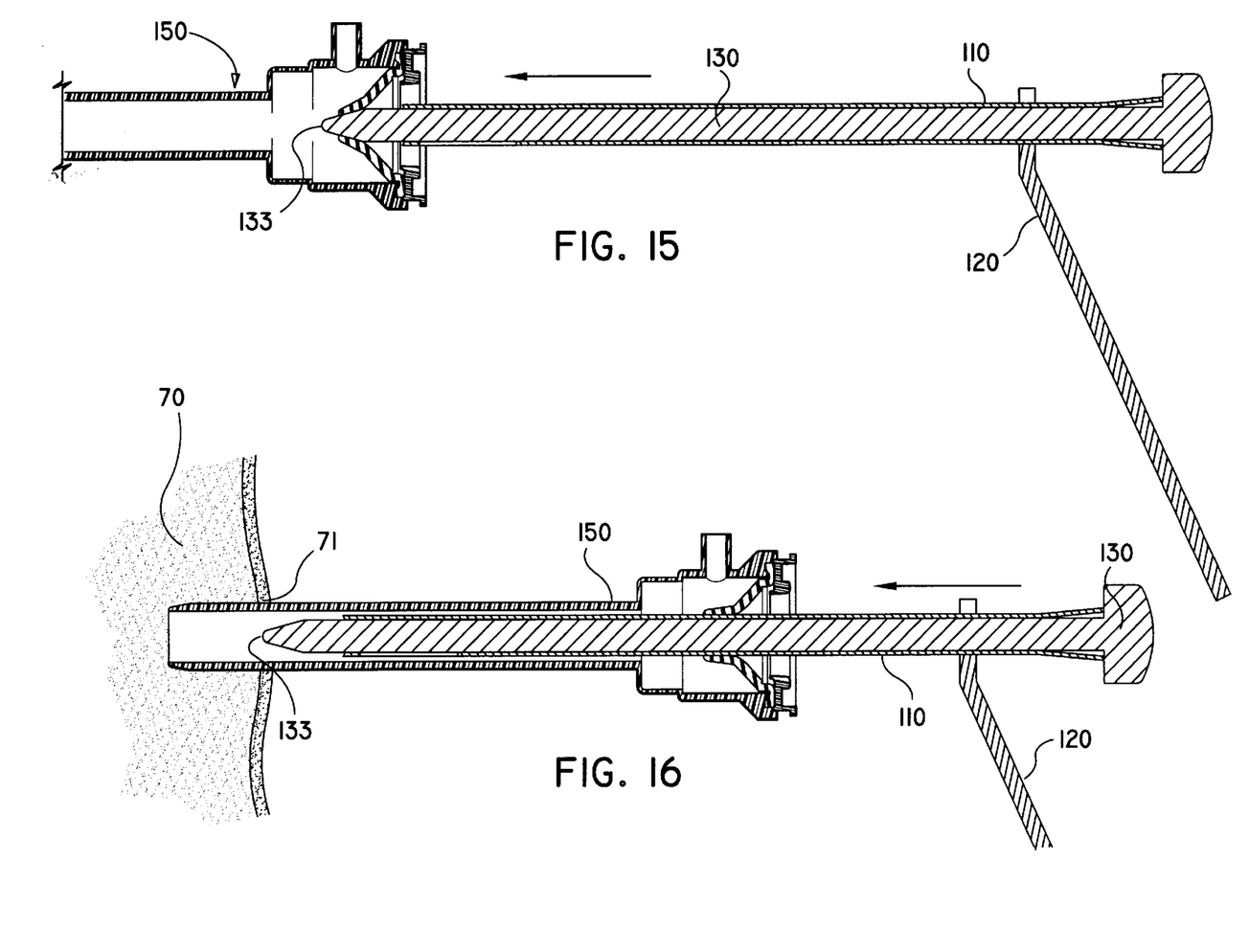
FIG. 15 is a sectional view showing placement of the obturator and drill guide in the cannula.
FIGS. 16 to 19 are sectional views sequentially illustrating the method of drilling a hole in bone and the placement of the suture anchor therein.

Obturator 130 is placed within the drill guide 110 and both are inserted through cannula 150 and into body tissue 70 to create a passageway through the soft tissue to access the bone. (FIGS. 15, 16). Obturator 130 is then removed leaving drill guide 110 inserted through the passageway in the soft tissue with the distal teeth 113 placed against the bone at the site to be drilled.

Figure 17:
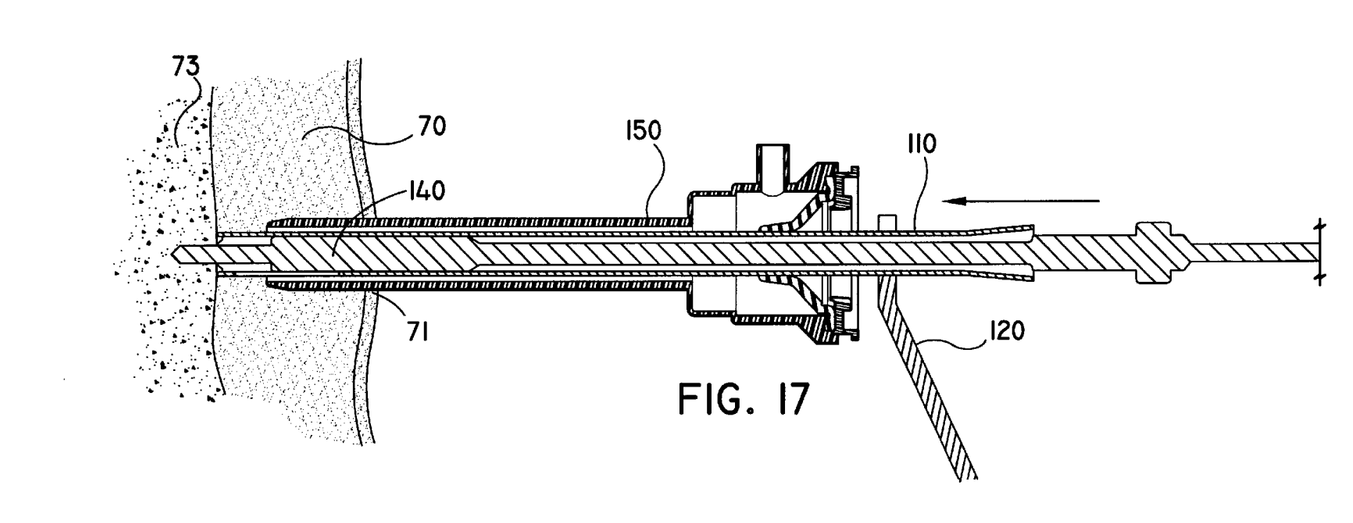

The drill bit 140 is then inserted in the drill guide and is used to create a hole 74 in the bone 73. (FIG. 17)

Figure 18:
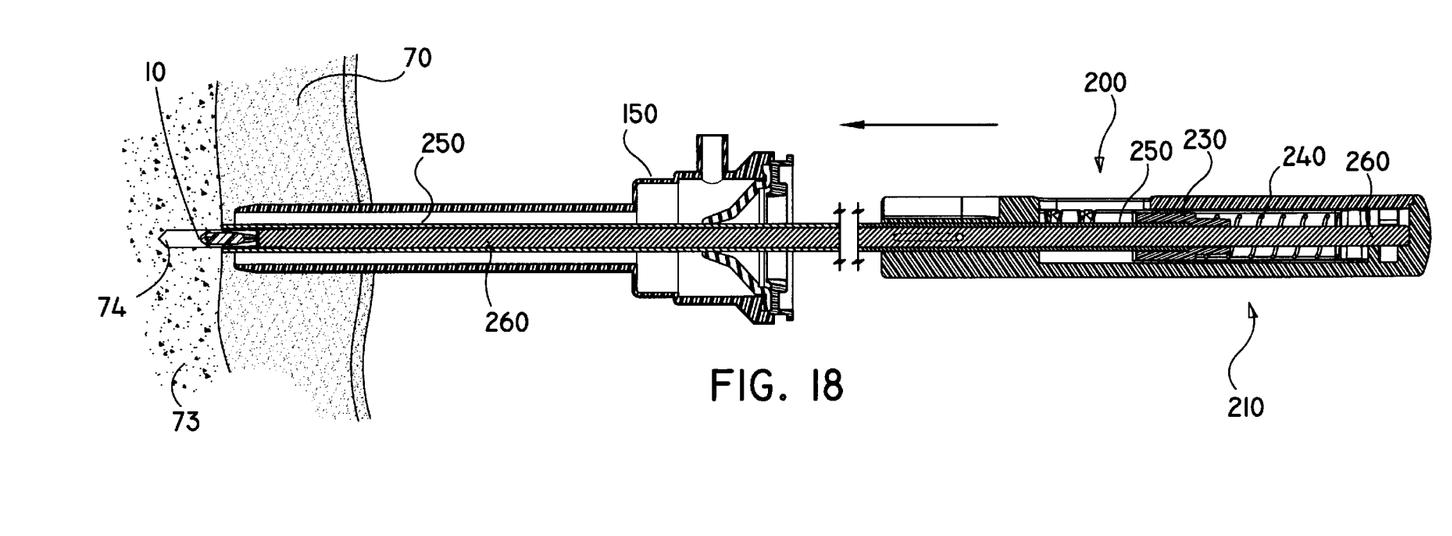
Figure 19:
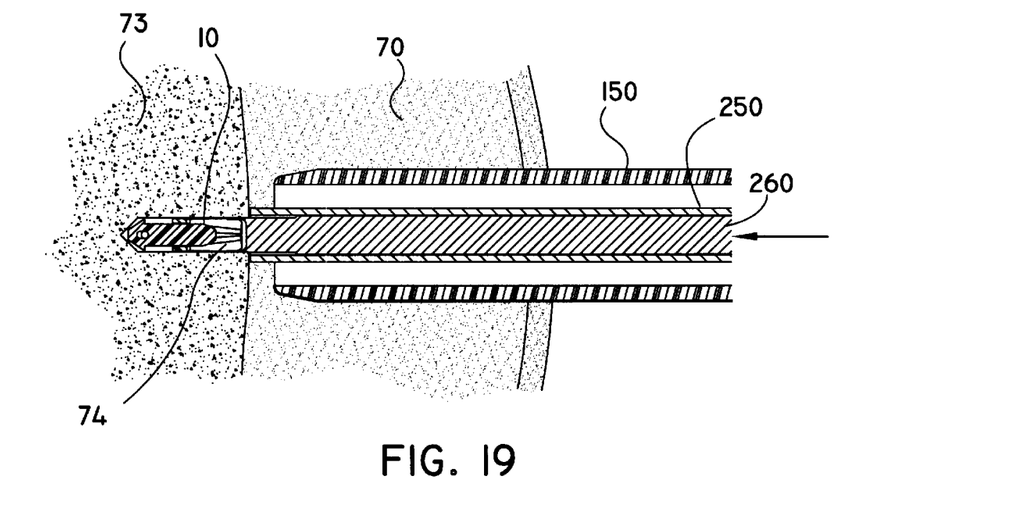
Figure 20:
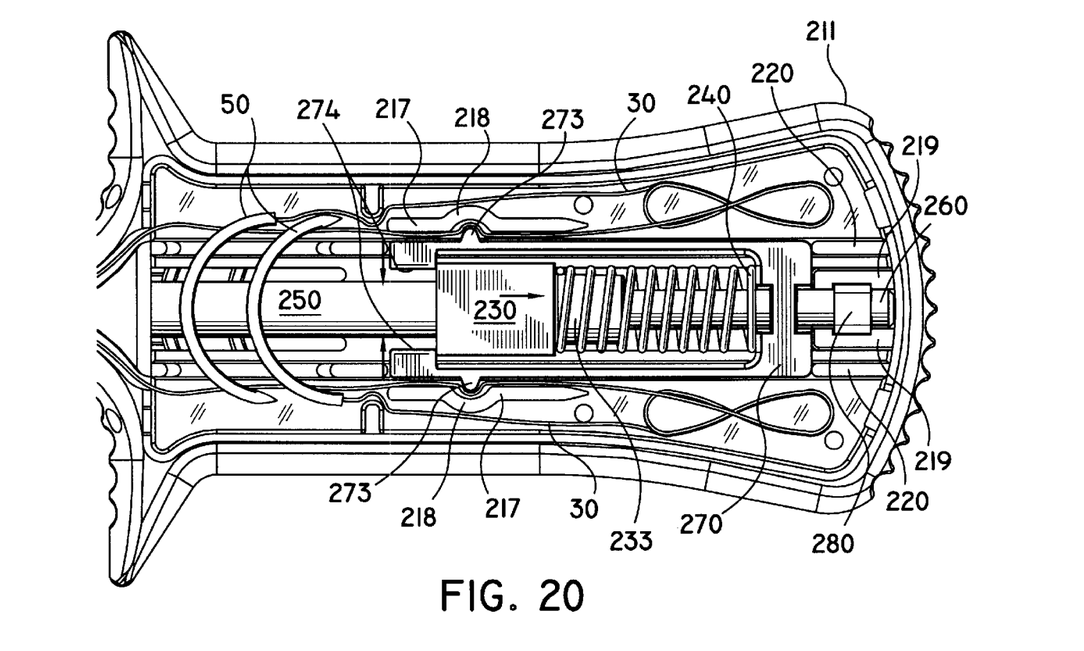
FIG. 20 is a top view of the handle portion of the suture anchor installation tool showing release of the suture.
Figure 21:
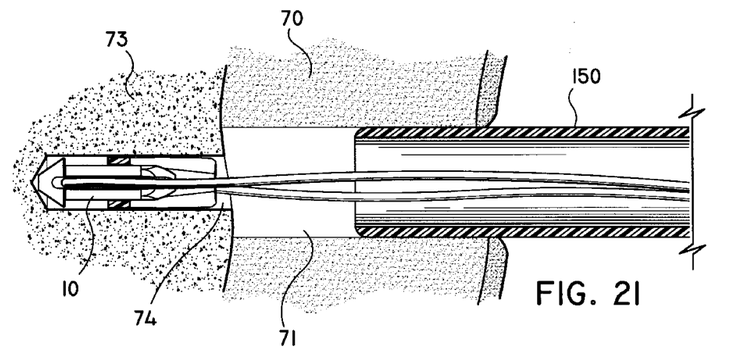
FIGS. 21 and 22 are sequential side sectional views illustrating setting of the suture anchor.
Figure 22:
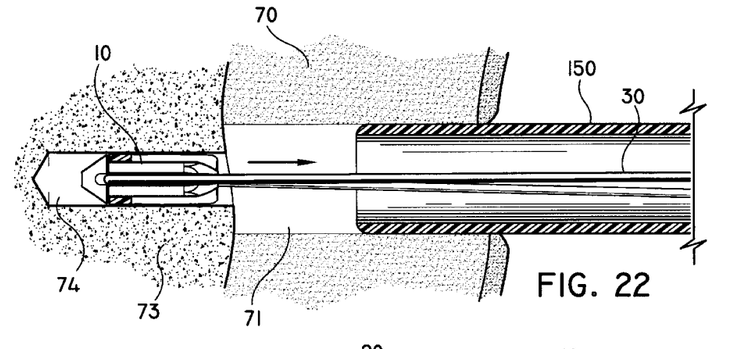
Figures 23, 24:
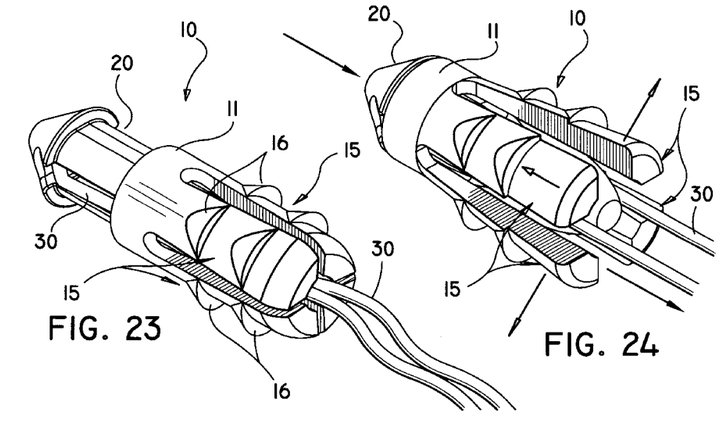
FIGS. 23 and 24 are perspective views illustrating actuation of the suture anchor to expand the legs.

Referring to FIG. 18, the drill bit and drill guide 110 are removed from cannula 150 and the distal end of the installation tool is then inserted into the cannula 150. Optionally, drill guide 110 can be left in place and the installation tool can be positioned within drill guide 110. The installation tool 200 is positioned such that suture anchor 10 is aligned with hole 74. The hole diameter is large enough to receive suture anchor 10 but smaller than the diameter of sheath tube 250. Referring to FIGS. 19, and 20, as the surgeon applies a distally directed force to installation tool 200 to advance suture anchor 10 into the hole in the bone, the adjacent bone structure pushes back on sheath tube 250. This action pushes cam cap 230 into the space between legs 272 of the pinch block, which spring inward, thereby locking the cam cap in a proximal position and releasing suture 30 from the pinch plate 217 such that suture 30 is no longer held in its initially taut manner. The installation tool 200 can then be withdrawn from the cannula 150, (FIG. 21) leaving the suture anchor 10 in place within hole 74. Referring to FIGS. 22, 23, and 24, the surgeon then removes needles 50 and suture 30 from handle 210 of the installation tool and pulls on the suture to expand the legs of the suture anchor (FIG. 24) and fix it securely within the bone. Optionally, the surgeon can actuate the suture anchor 10 prior to removal of installation tool 200 from the cannula, which approach may advantageously hold the suture anchor within the hole as the suture anchor is actuated. The suture lengths 30 can be tied to secure the soft tissue or prosthetic implant to the bone. For example, several suture anchors can be applied to the bone and the sutures of the various anchors can be knotted together to tie down the soft tissue.

It will be understood that various modifications may be made to the embodiments disclosed herein. The above description should not be construed as limiting, but merely as exemplifications of preferred embodiments. Those skilled in the art will envision other modifications within the scope and spirit of the claims appended hereto.

What is claimed is:

1. An apparatus for installing a suture anchor, which comprises:

a) a handle portion; and b) an elongated portion including a sheath tube having an axial bore and distal and proximal ends, and an inner rod slidably disposed within the bore of the sheath tube, the inner rod being fixedly mounted to the handle, and the sheath tube being mounted to the handle and movable with respect to the handle between a distal position and a proximal position, the sheath tube being resiliently biased to the distal position and movable to the proximal position in response to proximally directed force applied to the distal end of the sheath tube.

2. The apparatus of claim 1 wherein the inner rod has a distal end portion having an opening to releasably hold a suture anchor.

3. The apparatus of claim 1 wherein the sheath tube includes at least one longitudinal slot and the inner rod includes a pin extending into the longitudinal slot of the sheath tube to limit the relative motion between the inner rod and the sheath tube.

4. The apparatus of claim 1 wherein the handle includes at least one needle park.

5. The apparatus of claim 1 wherein the handle includes at least one pinch means for releasably holding a suture, the pinch means frictionally holding the suture when the sheath tube is in the distal position and releasing the suture in response to movement of the sheath tube to the proximal position.

6. The apparatus of claim 1 further including a plate and at least one leg in opposing relation to the plate, the leg being biased toward the wall to hold a suture therebetween when the sheath tube is in the distal position, and the leg resiliently moving away from the wall in response to movement of the sheath tube to the proximal position.

7. The apparatus of claim 1 further including a suture anchor which includes an elongated setting pin at least partially mounted within a longitudinal bore of a socket and slidably movable between a distal first position wherein at least a portion of the setting pin is distal to the socket and a proximal second position, the socket having at least two proximally pointing legs which are radially expandable in response to movement of the setting pin to said proximal second position, and the setting pin having a suture connected thereto.

8. The apparatus of claim 6 further including a suture anchor with a suture connected thereto wherein the suture is disposed longitudinally along an outside surface of the sheath tube in an initially taut configuration, a portion of the suture being disposed between the plate and the at least one leg.

9. The apparatus of claim 1 wherein the handle includes a spring for resiliently biasing the sheath tube to the distal position.

10. A system for installing a suture anchor, which comprises:
   a) means for drilling a hole of predetermined diameter into bone tissue;
   b) a suture anchor having a length of suture attached thereto;
   c) a suture anchor installation tool which includes
      i) a handle portion; and
      ii) an elongated portion including a sheath tube having an axial bore and distal and proximal ends, and an inner rod slidably disposed with the bore of the sheath tube, the inner rod being fixedly mounted to the handle, and the sheath tube being mounted to the handle and movable with respect to the handle between a distal position and a proximal position, the sheath tube being resiliently biased to the distal position and movable to the proximal position in response to proximally directed force of sufficient magnitude applied to the distal end of the sheath tube, the sheath tube having a portion with an outer diameter greater than the diameter of the hole in the bone.

11. The system of claim 10 wherein the suture anchor is releasably mounted to a distal end portion of the rod.

12. The system of claim 10 wherein the sheath tube includes at least one longitudinal slot and the inner rod includes a pin extending into the longitudinal slot of the sheath tube to limit the relative motion between the inner rod and the sheath tube.

13. The system of claim 10 wherein the handle includes at least one needle park.

14. The system of claim 10 wherein the means for drilling a hole in bone includes a guide tube and a drill bit movably disposed with the guide tube.

15. The system of claim 10 further including an obturator.

16. The system of claim 10 wherein the suture anchor includes an elongated setting pin at least partially mounted within a longitudinal bore of a socket and slidably movable between a distal first position wherein at least a portion of the setting pin is distal to the socket and a proximal second position, the socket having at least two proximally pointing legs which are radially expandable in response to movement of the setting pin to said proximal second position.

17. A method for applying a suture anchor to bone, comprising:
   a) drilling a hole of predetermined size into a mass of bone tissue;
   b) providing a suture anchor having a length of suture connected thereto;
   c) providing a suture anchor installation tool which includes
      i) a handle portion; and
      ii) an elongated portion including an sheath tube having an axial bore, and distal and proximal ends, and an inner rod slidably disposed with the bore of the sheath tube, the inner rod being fixedly mounted to the handle and having a distal end portion to which the suture anchor is releasably engaged, and the sheath tube being mounted to the handle and movable with respect to the handle between a distal position and a proximal position, the sheath tube being resiliently biased to the distal position and movable to the proximal position in response to proximally directed force of sufficient magnitude applied to the distal end of the sheath tube, the sheath tube having a portion with an outer diameter greater than the diameter of the hole in the bone;
   d) positioning the distal end of the sheath tube in conjunction with the hole in the bone such that the suture anchor is aligned with the hole in the bone;
   e) applying distally directed force to the installation tool, thereby advancing the suture anchor into the hole in the bone while moving the sheath tube proximally with respect to the handle.

18. The method of claim 17 further comprising the step of deploying the suture anchor in the hole.

19. The method of claim 18 wherein the suture anchor includes a setting pin connected at least partially mounted within a longitudinal bore of a socket and slidably movable between a distal first position wherein at least a portion of the setting pin is distal to the socket and a proximal second position, the socket having at least two legs which are radially expandable in response to movement of the setting pin to said proximal second position, the step of actuating the suture anchor comprising moving the setting pin to its proximal second position.

20. The method of claim 19 wherein the setting pin is moved to its proximal position by applying a proximally directed pulling force to the suture sufficient to move the setting pin to the proximal second position.

21. The method of claim 17 further including the steps of providing an obturator and forming an opening in soft body tissue in the vicinity of the bone mass prior to drilling a hole in the bone and inserting a cannula into the opening in the soft tissue.

22. The method of claim 21 wherein the step of drilling a hole of predetermined size into a mass of bone tissue comprises:
   placing a drill guide tube through the opening in the soft tissue formed by the obturator,
   positioning the drill guide tube with respect to the bone,
   inserting a drill bit through the drill guide tube into contact with the bone tissue, and,
   drilling the bone tissue with the drill bit.

* * * * *